US010100352B2

(12) United States Patent
Tanaka et al.

(10) Patent No.: US 10,100,352 B2
(45) Date of Patent: Oct. 16, 2018

(54) DNA CHIP WITH MICRO-CHANNEL FOR DNA ANALYSIS

(71) Applicants: Panasonic Corporation, Osaka (JP); IMEC vzw, Leuven (BE)

(72) Inventors: Hiroyuki Tanaka, Nara (JP); Maki Hiraoka, Nara (JP); Benjamin Jones, Leuven (BE); Paolo Fiorini, Leuven (BE)

(73) Assignees: PANASONIC CORPORATION, Osaka (JP); IMEC VZW, Leuven (BE)

( * ) Notice: Subject to any disclaimer, the term of this patent is extended or adjusted under 35 U.S.C. 154(b) by 469 days.

(21) Appl. No.: 14/196,293

(22) Filed: Mar. 4, 2014

(65) Prior Publication Data

US 2014/0186846 A1 Jul. 3, 2014

Related U.S. Application Data

(63) Continuation of application No. PCT/JP2013/062310, filed on Apr. 19, 2013.

(30) Foreign Application Priority Data

Apr. 20, 2012 (JP) ................. 2012-096885

(51) Int. Cl.
   *C12Q 1/686* (2018.01)
   *B01L 7/00* (2006.01)
   *B01L 3/00* (2006.01)

(52) U.S. Cl.
   CPC ........ *C12Q 1/686* (2013.01); *B01L 3/502707* (2013.01); *B01L 3/502715* (2013.01);
   (Continued)

(58) Field of Classification Search
   None
   See application file for complete search history.

(56) References Cited

U.S. PATENT DOCUMENTS

| 7,351,303 B2* | 4/2008 | Liu ..................... B01F 13/0827 156/290 |
| 2005/0142565 A1* | 6/2005 | Samper ................ B01L 3/5027 435/6.11 |

(Continued)

FOREIGN PATENT DOCUMENTS

JP   2011-522219   7/2011

OTHER PUBLICATIONS

M. Op de Beeck, W. De Malsche, M. Hiraoka, P. Fiorini, L. Zhang, J. Op de Beeck, B. Majeed, H. Tanaka, D. Sabuncuoglu Tezcan, G. Desmet, D. Ueda, C. Van Hoof, I. Yamashita, Design and Fabrication of a Biomedical Lab-on-Chip System for SNP Detection in DNA, 2010 IEDM Conference, San Francisco, Dec. 6-8, 2010, pp. IEDM10-824-IEDM10-827 (36.3.1-36.*

(Continued)

*Primary Examiner* — Suchira Pande
(74) *Attorney, Agent, or Firm* — Wenderoth, Lind & Ponack, L.L.P.

(57) ABSTRACT

Provided is a DNA chip with micro-channel for DNA analysis, which has a structure in which a silicon layer (chip A) and a plastic layer (chip B) are laminated, wherein the chip A includes at least two PCR reactors connected in series in a micro-channel, and a filter between the PCR reactors, the chip B includes a reagent, a liquid delivery mechanism and a sensor in a micro-channel, and the reagent, liquid delivery mechanism and sensor can be changed according to a kind of an analyte and an object to be detected.

3 Claims, 13 Drawing Sheets

Specification includes a Sequence Listing.

(52) U.S. Cl.
CPC ......... *B01L 7/52* (2013.01); *B01L 2300/0636* (2013.01); *B01L 2300/0681* (2013.01); *B01L 2300/0816* (2013.01); *B01L 2300/0861* (2013.01); *B01L 2300/0883* (2013.01); *B01L 2400/086* (2013.01)

(56) References Cited

U.S. PATENT DOCUMENTS

| | | |
|---|---|---|
| 2008/0112854 A1 | 5/2008 | Park et al. |
| 2009/0023610 A1 | 1/2009 | Peytavi |
| 2009/0227476 A1 | 9/2009 | Malcolm |
| 2009/0269767 A1 | 10/2009 | Soderlund et al. |
| 2013/0078155 A1 | 3/2013 | Jones et al. |

OTHER PUBLICATIONS

Anderson et al. (2000) Nucl. Acids Res. vol. 28 No. 12 e 60 (Year: 2000).*

English translation of the International Preliminary Report on Patentability and Written Opinion dated Oct. 21, 2014.

Extended European Search Report dated Nov. 26, 2015 in corresponding European patent application No. 13 77 8172.

Alexis F. Sauer-Budge et al., "Low Cost and manufacturable complete microTAS for detecting bacteria", Lab on a Chip, vol. 9, No. 19, Jan. 1, 2009, p. 2803, XP055094146.

International Search Report dated Jul. 30, 2013 in International (PCT) Application No. PCT/JP2013/062310.

P. F. Man et al., "Microfluidic Plastic Capillaries on Silicon Substrates: A New Inexpensive Technology for Bioanalysis Chips", Micro Electro Mechanical Systems, 1997, MEMS '97, Proceedings, IEEE., Tenth Annual International Workshop on Jan. 26, 1997, pp. 311-316.

M. Palmieri et al., "Advanced Microfluidic Packaging for Molecular Diagnostics", $43^{rd}$ International Symposium on Microelectronics 2010, (IMAPS 2010), pp. 36-41.

D. S. Lee et al., "Bulk-Micromachined Submicroliter-Volume PCR Chip with very Rapid Thermal Response and Low Power Consumption", Lab on a Chip, Mar. 29, 2004, vol. 4, No. 4, pp. 401-407.

I. Yamashita et al., Realizing Rapid On-site SNP Diagnosis, Panasonic Technical Journal, Oct. 15, 2011, col. 57, No. 3, pp. 21-26.

B. Majeed et al., "Silicon Based System for Single-Nucleotide-Polymorphism Detection: Chip Fabrication and Thermal Characterization of Polymerase Chain Reaction Microchamber", Japanese Journal of Applied Physics, Apr. 20, 2012, vol. 51, 04DL01 (9 pages).

B. Majeed et al., "Silicon Micro-Pillar Filter Fabrication for DNA Separation in Lab-on-Chip System", Electronics Packaging Technology Conference (EPTC), 2012 IEEE 14th, Dec. 5, 2012, pp. 52-56.

S. L. Marasso et al., "A Multilevel Labe on Chip Platform for DNA Analysis", Biomed Microdevices, 2011, vol. 13, pp. 19-27.

* cited by examiner

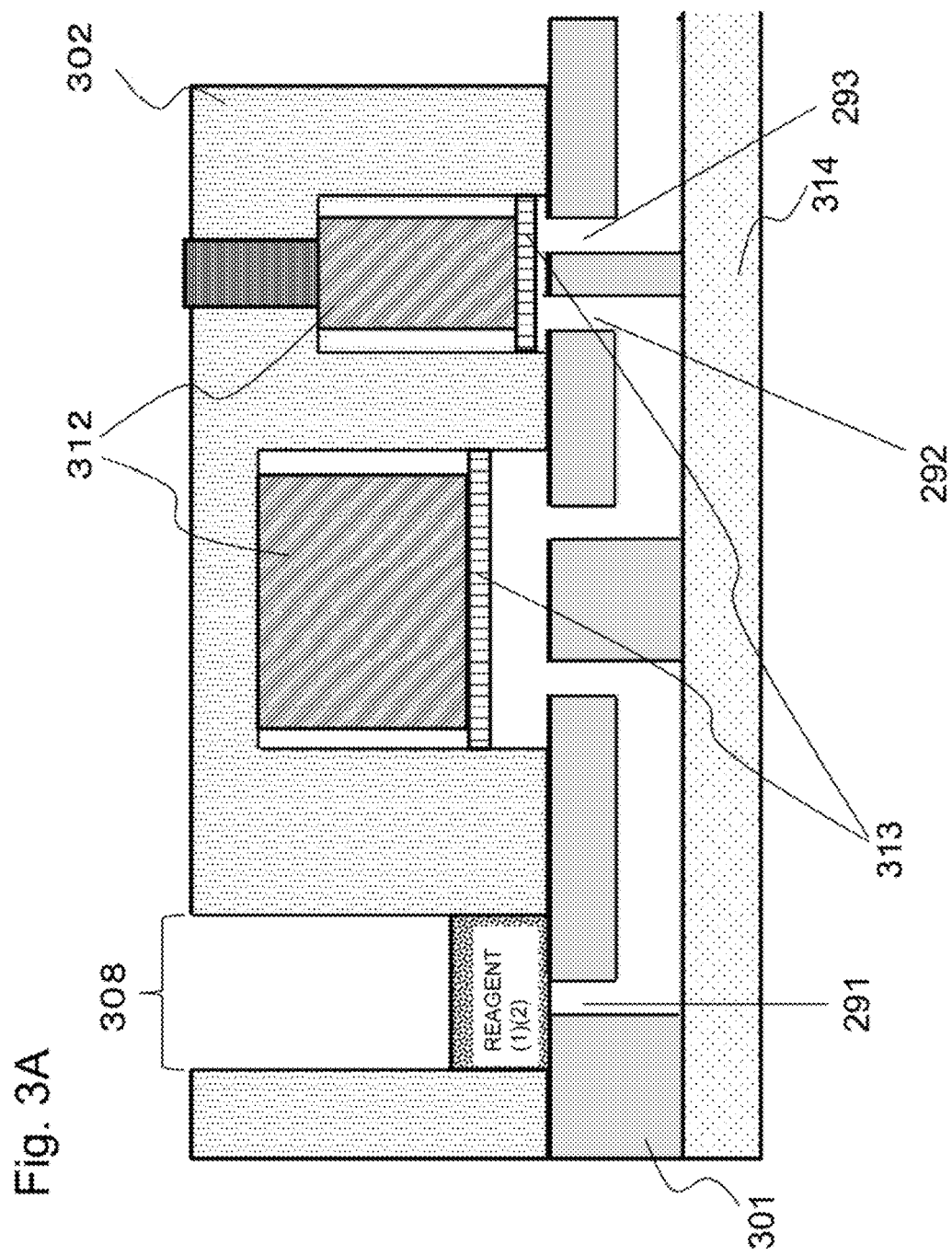

Fig. 8

| | PURPOSE | ANALYTE | REAGENT (1) | REAGENT (2) | REAGENT (3) | SENSOR |
|---|---|---|---|---|---|---|
| EXAMPLE 1 | AMPLIFICATION OF DNA FROM GENOME | HUMAN GENOME | (A) | - | - | - |
| EXAMPLE 2 | AMPLIFICATION OF DNA FROM BLOOD | HUMAN BLOOD | (B) | - | - | - |
| EXAMPLE 3 | ALLELE-SPECIFIC DNA AMPLIFICATION | HUMAN BLOOD | (B) | (C) | - | - |
| EXAMPLE 4 | SNP SENSING | HUMAN BLOOD | (B) | (C) | (D) | PYROPHOSPHORIC ACID SENSOR |

DNA CHIP WITH MICRO-CHANNEL FOR DNA ANALYSIS

CROSS-REFERENCE TO RELATED APPLICATIONS

This is a continuation application of International Application No. PCT/JP2013/062310, with an international filing date of Apr. 19, 2013, which claims priority of Japanese Patent Application No. 2012-96885 filed on Apr. 20, 2012, the contents of which is incorporated herein by reference.

BACKGROUND

1. Technical Field

The present disclosure relates to a chip with micro-channel which is formed on a laminated substrate of silicon and plastic. More particularly, the present disclosure relates to a chip with micro-channel which integrally has functionalities for quickly and conveniently extracting and amplifying desired DNA from an analyte containing a gene, or detecting a sequence of the DNA.

2. Related Art

In recent years, progress of genetic diversity analysis and expression analysis has been outstanding owing to improvement of DNA analysis techniques. Particularly in medical fields, the relationship between diseases and genes attracts attention. For example, by analyzing information of individual genetic information (specific DNA sequence) related to a disease, suitable treatment or administration can be carried out for each individual patient (personalized medicine). In personalized medicine, in situ diagnostics are most desirable, and speedy and convenient techniques with a strong aspect of POCT (Point of Care Testing) are desired. Therefore, it is strongly desired to realize a device capable of quickly and conveniently extracting and amplifying DNA of a gene to be analyzed from a collected analyte such as blood, and detecting a sequence of the DNA.

As one of means to meet these requirements, micro-total analysis systems (μTAS) (also called as a lab-on-chip) have attracted attention in recent years. In the μTAS or lab-on-chip, micro-channels and ports having fine structures in a micrometer order are provided in a substrate, and various kinds of operations including mixing, extraction, refinement, chemical reaction and/or analysis of a substance, and so on can be performed within the structures. The μTAS has been partially put into practical use. Since various kinds of operations are performed within fine structures, the μTAS has the following features compared to the same type of device in common size: (1) the use amounts of a sample and a reagent are remarkably small; (2) the analysis time is short; (3) the sensitivity is high; (4) it can be carried to an actual spot to perform analysis on the spot; and (5) it is disposable. Structures prepared for the purpose described above and having fine structures such as micro-channels and ports in a substrate are collectively called as a chip with micro-channel or device with micro-fluid.

For analyzing DNA in a gene in an analyte in a short time using a chip with micro-channel, it is necessary to incorporate functionalities of extraction and amplification into the chip, and realization of a fine filter for separating impurities such as blood cells and a PCR (polymerase chain reaction) capable of increasing and decreasing the temperature at a high speed is required. In addition, convenience in use is required, and it is therefore desirable to be able to stably retain an analyte, a reagent and the like in the chip. Further, in personalized medicine applications, it is desirable to have a configuration that allows treatment from blood, and to be able to sense a single base-multiple system (SNP) in DNA at a detection section. That is, it is desired to realize a versatile chip that can flexibly adapt to operating conditions.

However, due to limitations on the nature of a material of a substrate that forms a chip with micro-channel, it is difficult to realize a device with micro-channel which can meet all the foregoing requirements. The reason for this will be described below.

Plastic or silicon is used as a material of a substrate of a chip with micro-channel. The plastic substrate has such a feature that material costs are relatively low, it is easy to perform cutting processing, and affinity with a biological/bio material is relatively high, so that a reagent is easily retained, and so on. On the other hand, however, the plastic substrate has a problem that it is not suitable for formation of a fine filter structure for separating impurities such as blood cells and for formation of a thermal reactor for which it is required to increase and decrease the temperature at a high speed, such as a PCR (polymerase chain reaction), because it is difficult to process fine structures in a sub-micrometer order and the thermal conductivity of the material is not satisfactory. The silicon substrate is suitable for formation of a fine filter structure and a PCR thermal reactor because fine structures are easily formed by a semiconductor lithography technique and the thermal conductivity is higher by 2 to 3 order of magnitude than that of plastic. On the other hand, however, there is the problem that the unit price of the material is high in comparison with plastic, and the silicon substrate is not suitable for storage of a reagent because affinity between the surface of silicon and a biological/bio material is not necessarily high, and therefore non-specific adsorption of a protein and DNA occurs. As described above, plastic and silicon have mutually contradictory advantages and disadvantages, and with a configuration using a substrate of only one of silicon and plastic, conditions required for a chip with micro-channel for used in DNA analysis cannot be adequately satisfied.

As means for solving the above-described problems, a chip with micro-channel has been proposed in which a silicon substrate and a plastic substrate are laminated (see, for example, BioMed Microdevice (2011), 13:19-27 and Proceeding of 43rd International Symposium on Microelectronics (IMAPS 2010), 000036).

In BioMed Microdevice (2011), 13:19-27, a structure is disclosed in which plastic and silicon are laminated, and a chip with micro-channel and a liquid delivery section are arranged separately. In this method, however, the temperature cannot be increased and decreased at a high speed because a thermal reactor is formed of a plastic material, and also the reactor is isolated from silicon as a heating surface with a glass substrate interposed therebetween, so that it is very difficult to secure a thermal contact, leading to poor heat conduction. Further, the method cannot be used conveniently because it employs a structure in which an analyte and a reagent are supplied from outside the chip. Therefore, the method has the problem that it is not suitable for quick and convenient treatments.

In Proceeding of 43rd International Symposium on Microelectronics (IMAPS 2010), 000036, a structure is disclosed in which a thermal reactor is formed in a silicon chip, and an analyte and a reagent are supplied from the inside of the chip. Therefore, increasing and decreasing of temperature at a high speed and convenient treatments can be achieved. However, in this method, a sensor is confined to a DNA micro-array chip, and this is formed on a silicon substrate identical to that of the thermal reactor (PCR). That is, steps of producing the thermal reactor and the sensor should be successively performed, and the design cannot be flexibly changed according to an intended purpose. Further, only one thermal reactor is mounted, and only a refined genome can be used as an analyte, so that a treatment from blood cannot be performed. The method cannot adapt to applications that require two stages of PCRs: a PCR intended for extracting a genome to be analyzed from blood and a PCR intended for selectively amplifying DNA based on presence/absence of a SNP in the object to be analyzed. Further, a filter for separating and removing blood-derived blood cells generated during the treatment is not present. That is, the method has the problem that it cannot adapt to applications of detection from blood, and is therefore poor in versatility.

That is, the disclosed methods have the major problem that both a configuration of a high-performance chip with micro-channel which is necessary to perform DNA analysis quickly and conveniently and a configuration of a chip with micro-channel which has high versatility cannot be achieved.

The present disclosure has been made for solving the problems described above. One non-limiting and exemplary embodiment provide a DNA chip with micro-channel for DNA analysis, which performs extraction/amplification of DNA or detection of a sequence of the DNA quickly and conveniently and which has high versatility.

SUMMARY

In one general aspect, the techniques disclosed here feature: a DNA chip with micro-channel for DNA analysis of DNA included in an analyte according to PCR method, the DNA chip includes:
  a first layer (101) made of silicon; and
  a second layer (102) made of plastic,
  wherein the second layer (102) is formed on the first layer (101), and the second layer (102) is configured to be changeably selected depending on a kind of the analyte and an object to be analyzed,
  the first layer (101) includes:
  at least four openings (291, 292, 293, 294);
  at least two PCR reactors (203, 204, 403, 404); and
  a micro channel connecting among the openings and the PCR reactors,
  the second layer (102) includes:
  a pump (312); and
  a sensor (315),
  wherein a reagent (1, 2) is provided to overlap at least one opening included the plurality of openings when one sees from normal direction of the first layer (101),
  the pump (312) overlaps at least two openings included the plurality of openings when one sees from normal direction of the first layer (101),
  the pump supplies the reagent to the PCR reactors via the micro channel such that mixture of the reagent and the analyte is supplied to the PCR reactors; and
  the mixture is transported to the sensor from the PCR reactors such that the sensor analyzes DNA included in the analyte according to PCR method.

By providing the structure described above, a PCR capable of increasing and decreasing the temperature at a high speed can be incorporated, and an analyte and reagent can be manipulated and stored within the chip, so that DNA analysis can be performed quickly and conveniently. Also, PCR amplification and filtering with not only a genome but also blood can be performed by providing the above-described structure. Therefore, multiple (at least four) applications: (1) extraction and amplification of DNA from a genome, (2) extraction and amplification of DNA from blood, (3) extraction and amplification of allele-specific DNA from a genome or blood and (4) detection of a SNP from a genome or blood, etc. can be accommodated only by changing the configurations of a reagent, a liquid delivery mechanism and a sensor in a chip B with the configuration of a chip A unchanged. That is, a high versatility can be imparted to the chip.

According to the present disclosure, extraction and amplification of DNA or detection of a sequence of the DNA can be performed quickly and conveniently in a DNA chip with micro-channel for DNA analysis, and the chip can be used for a variety of applications, leading to enhancement of versatility.

Additional benefits and advantages of the disclosed embodiments will be apparent from the specification and figures. The benefits and/or advantages may be individually provided by the various embodiments and features of the specification and drawings disclosure, and need not all be provided in order to obtain one or more of the same.

BRIEF DESCRIPTION OF THE DRAWINGS

The present disclosure will become readily understood from the following description of non-limiting and exemplary embodiments thereof made with reference to the accompanying drawings, in which like parts are designated by like reference numeral and in which:

FIG. 3A is a sectional schematic view showing the components of the DNA chip with micro-channel for DNA analysis according to the present disclosure, the sectional view including a reagent, a pump and a valve;

FIG. 8 is a table of examples, which shows versatility of the present disclosure;

DETAILED DESCRIPTION

Figure 1:
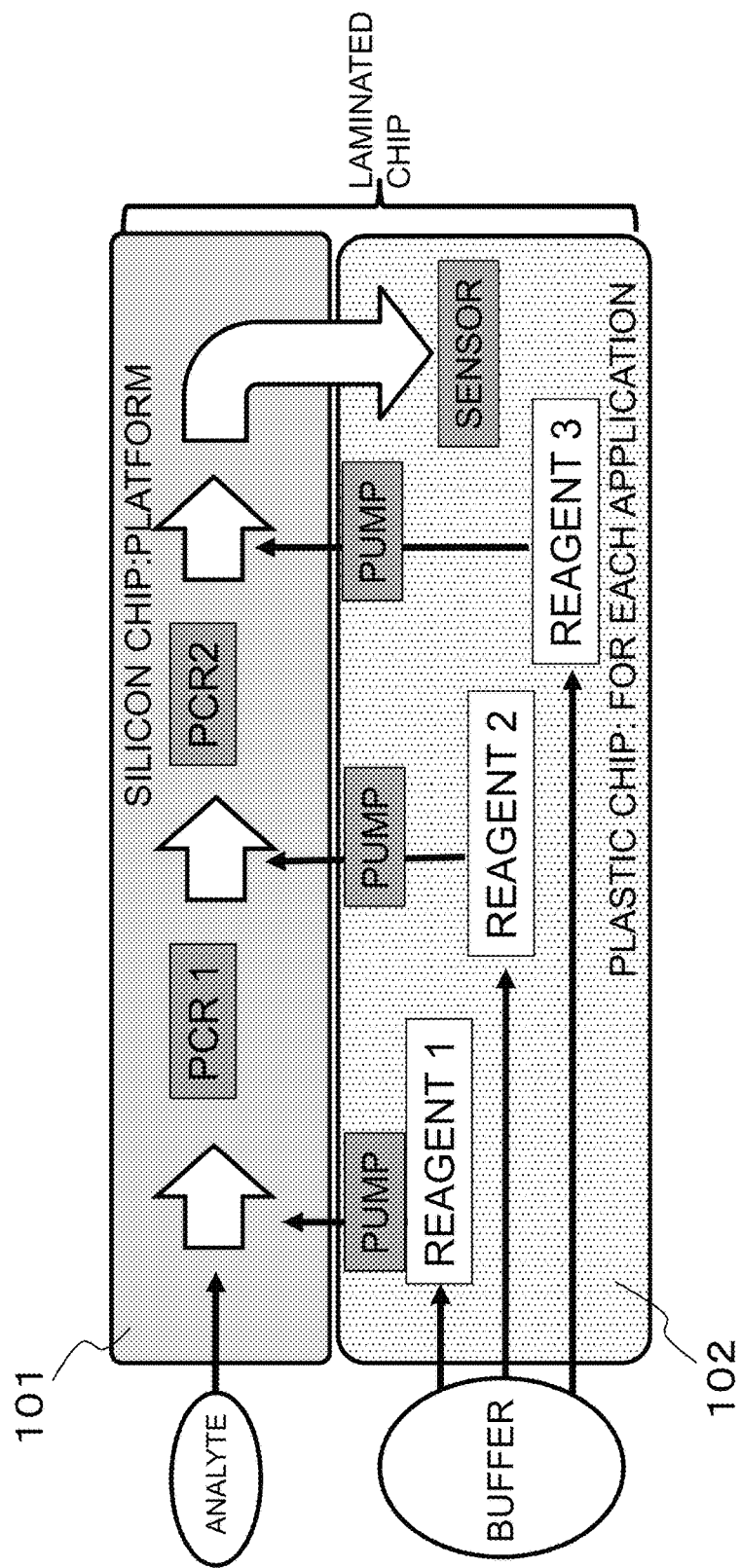
FIG. 1 is a general conceptual view of a DNA chip with micro-channel for DNA analysis according to the present disclosure.

According to a first aspect of the present disclosure, a DNA chip with micro-channel for DNA analysis of DNA included in an analyte according to PCR method, the DNA chip includes:
  a first layer (101) made of silicon; and
  a second layer (102) made of plastic,
  wherein the second layer (102) is formed on the first layer (101), and the second layer (102) is configured to be changeably selected depending on a kind of the analyte and an object to be analyzed,
    the first layer (101) includes:
    at least four openings (291, 292, 293, 294);
    at least two PCR reactors (203, 204, 403, 404);
    at least one filter (206) provided between PCR reactors; and
    a micro channel connecting among the openings, the PCR reactors, and the at least one filter,
    the second layer (102) includes:
    a pump (312); and
    a sensor (315),
  wherein a reagent (1, 2) is provided to overlap at least one opening (291) included in the four openings when one sees from normal direction of the first layer (101),
  the pump (312) overlaps at least two openings (292, 293) included in the four openings when one sees from normal direction of the first layer (101),
  the pump supplies the reagent to the PCR reactors via the micro channel such that mixture of the reagent and the analyte is supplied to the PCR reactors; and
  the mixture is transported from the PCR reactor to the sensor via at least one opening (294) included in the four openings such that the sensor analyzes DNA included in the analyte.

A DNA chip with micro-channel for DNA analysis according to a second aspect is the chip with micro-channel for DNA analysis according to the first aspect, wherein a peripheral area made of silicon around the PCR reactor may be hollowed out except for an area connected to the micro channel.

When the outer peripheral area of the PCR reactor is mostly hollowed out as described above to thermally isolate the peripheral area, release of heat to the outer peripheral area and absorption of heat from the outer peripheral area can be suppressed, and therefore a PCR capable of increasing and decreasing the temperature at a higher speed can be achieved, so that DNA analysis can be performed more quickly.

A DNA chip with micro-channel for DNA analysis according to a third aspect is the chip with micro-channel for DNA analysis according to the first aspect, wherein the filter may include a plurality of column pillars made of silicon formed by etching, a space between column pillars ranging from 1 micrometer to 10 micrometers.

When the space between pillars ranges from 1 micrometer to 10 micrometers as described above, unnecessary blood cell components fragmented by the PCR reactor can be efficiently removed with a filter without causing the filter to be clogged upon blood being used as an analyte.

A DNA chip with micro-channel for DNA analysis according to a fourth aspect is the chip with micro-channel for DNA analysis according to the first aspect, wherein a polymer actuator may be used as the liquid delivery mechanism.

When a polymer actuator is used as a liquid delivery mechanism (e.g. pump), a high generative force is obtained for delivering a liquid, and therefore a filter is hard to be clogged with analyte-derived substances. Further, when a polymer actuator is used as a liquid delivery mechanism (e.g. valve), a high pressure resistance is obtained for stopping liquid delivery, and therefore leakage to a channel can be suppressed. Consequently, stable chip operations can be performed.

A DNA analysis method of DNA included in an analyte according to PCR method according to a fifth aspect is a DNA analysis method of DNA included in an analyte according to PCR method, including:
  (a) providing a first layer (101) made of silicon and a plurality of second layers (102) made of plastic,
    the first layer (101) including:
    at least four openings (291, 292, 293, 294);
    at least two PCR reactors (203, 204, 403, 404);
    at least one filter (206) provided between PCR reactors; and
    a micro channel connecting among the openings, the PCR reactors, and the filter,
    each second layer (102) including:
    a reagent (1, 2) to be used in the PCR method;
    a pump (312); and
    a sensor (315),
  (b) selecting one of the second layers (102) depending on a kind of the analyte and an object to be analyzed from the plurality of second layers (102),
  (c) forming the second layer selected in (b) on the first layer (101) to obtain a DNA chip with micro-channel,
  wherein the reagent (1, 2) overlaps at least one opening (291) included in the four openings when one sees from normal direction of the first layer (101), and
  the pump (312) overlaps at least two openings (292, 293) included in the four openings when one sees from normal direction of the first layer (101),
  (d) supplying the analyte to an inside of the DNA chip with micro-channel;
  (e) supplying the reagent to the PCR reactors via the micro channel by using the pump such that mixtures of the reagent and the analyte are supplied to the PCR reactors;
  (f) performing PCR method to obtain PCR products in the PCR reactor;
  (g) transporting the PCR products obtained in (f) from the PCR reactor to the sensor via at least one opening (294) included in the four openings; and
  (h) detecting the PCR products by using the sensor to analyze DNA included in the analyte.

A DNA analysis method of DNA included in an analyte according to PCR method by using a DNA chip with a micro-channel according to a sixth aspect is a DNA analysis method of DNA included in an analyte according to PCR method by using a DNA chip with a micro-channel, including:
  (a') providing a DNA chip with micro-channel;
  the DNA chip including:
  a first layer (101) made of silicon; and
  a second layer (102) made of plastic,
  wherein the second layer (102) is formed on the first layer (101),
    the first layer (101) includes:
    at least four openings (291, 292, 293, 294);
    at least two PCR reactors (203, 204, 403, 404);
    at least one filter (206) provided between PCR reactors; and
    a micro channel connecting among the openings, the PCR reactors, and the at least one filter, the second layer (102) includes:
- a reagent (1, 2) to be used in the PCR method;
- a pump (312); and
- a sensor (315),
  - wherein the reagent (1, 2) overlaps at least one opening (291) included in the four openings when one sees from normal direction of the first layer (101), and
  - the pump (312) overlaps at least one opening (292, 293) included in the four openings when one sees from normal direction of the first layer (101), (d) supplying the analyte to an inside of the DNA chip with micro-channel for DNA analysis;

(e) supplying the reagent to the PCR reactors via the micro channel by using the pump such that mixtures of the reagent and the analyte are supplied to the PCR reactors;

(f) performing PCR method to obtain PCR products in the PCR reactor;

(g) transporting the PCR products obtained in (f) from the PCR reactor to the sensor via at least one opening (294) included in the four openings; and (h) detecting the PCR products by using the sensor to analyze DNA included in the analyte.

Embodiments of the present disclosure will be described below with reference to the drawings.

Embodiment 1

FIG. 1 is a general conceptual view of a chip with micro-channel according to the present disclosure. The DNA chip with micro-channel for DNA analysis in the present disclosure has a structure in which a silicon layer 101 (chip A) and a plastic layer 102 (chip B) are laminated. The chip A includes at least two PCR reactors connected in series in a micro-channel, and at least one filter including a plurality of silicon pillars between the PCR reactors, the chip B includes a reagent, a liquid delivery mechanism and a sensor in a micro-channel, and the reagent, liquid delivery mechanism and sensor can be changed according to a kind of an analyte and an object to be detected. Throw of an analyte and a reagent and treatments proceed in order along the arrow in FIG. 1.

Figure 2:
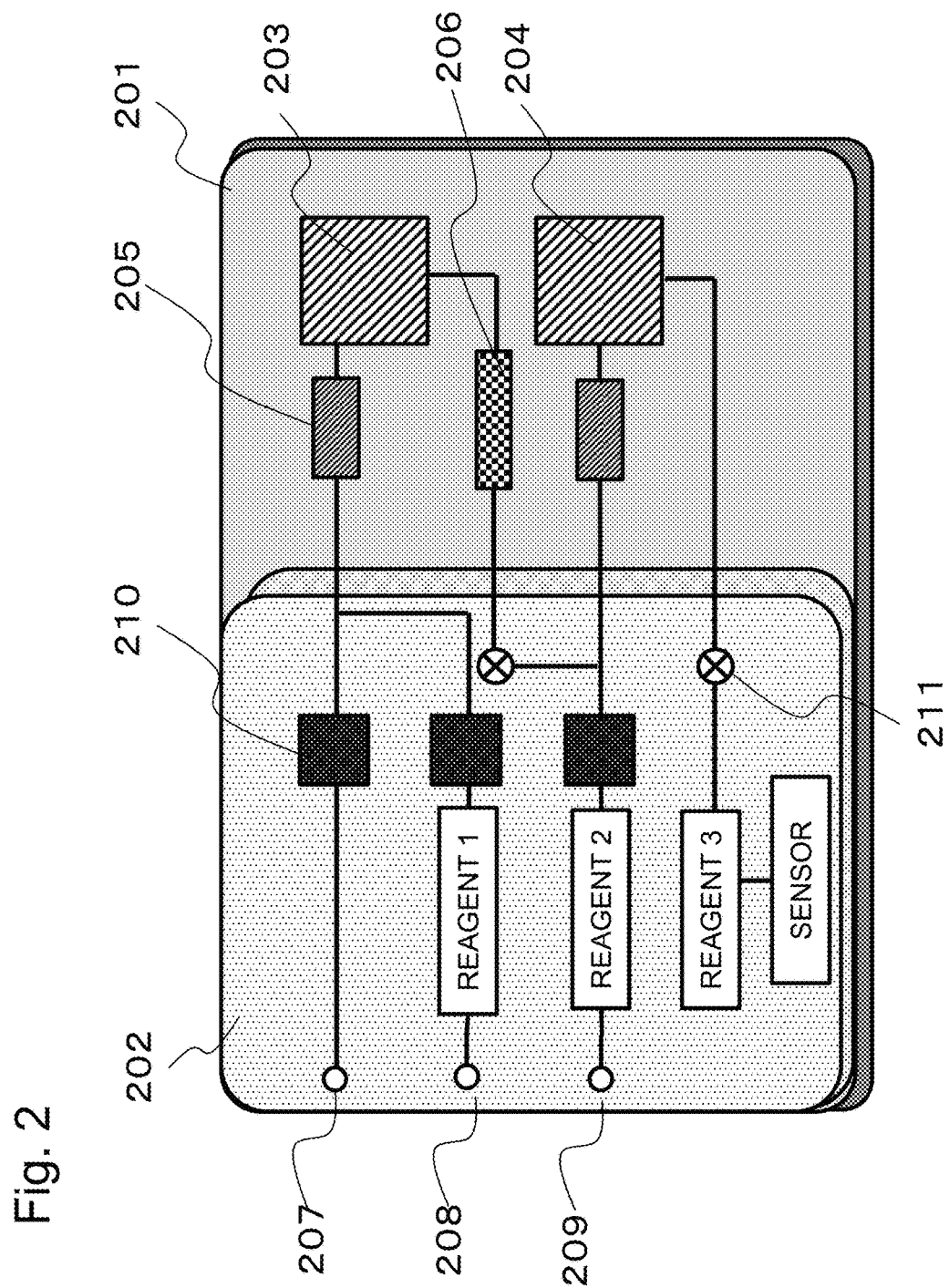
FIG. 2 is a schematic view showing components of the DNA chip with micro-channel for DNA analysis according to the present disclosure.

FIG. 2 is a schematic view showing components of the DNA chip with micro-channel for DNA analysis according to the present disclosure. The material of the chip A: 201 is silicon, a channel and a structure are engraved on a silicon substrate by photolithography and RIE (reactive ion gas etching), a PCR 1: 203 and PCR 2: 204, and also a mixer 205 and a filter 206 are formed, and connection is established as in the figure.

The material of the chip B: 202 is plastic, for example, PMMA (polymethylmethacrylate resin) or PDMS (polydimethylsiloxane) may be used. Further, an adhesive layer or elastomer may be used for a connection area with the silicon layer. As the reagent, reagents (1) and (2) such as a primer and polymerase which are used for reaction in the PCR reactors, and also a reagent (3) which is used in the sensor are arranged in the chip. The analyte is injected through a hole 207, and the reagents (1) and (2) are injected through holes 208 and 209, respectively. The reagent may be freeze-dried, and dissolved by pouring a buffer solution when used. The chip B: 202 has a liquid delivery mechanism, where a pump 210 and a valve 211 are arranged to provide a function of pouring the reagent into the chip and control the input of the reagent and timing.

Figure 3B:
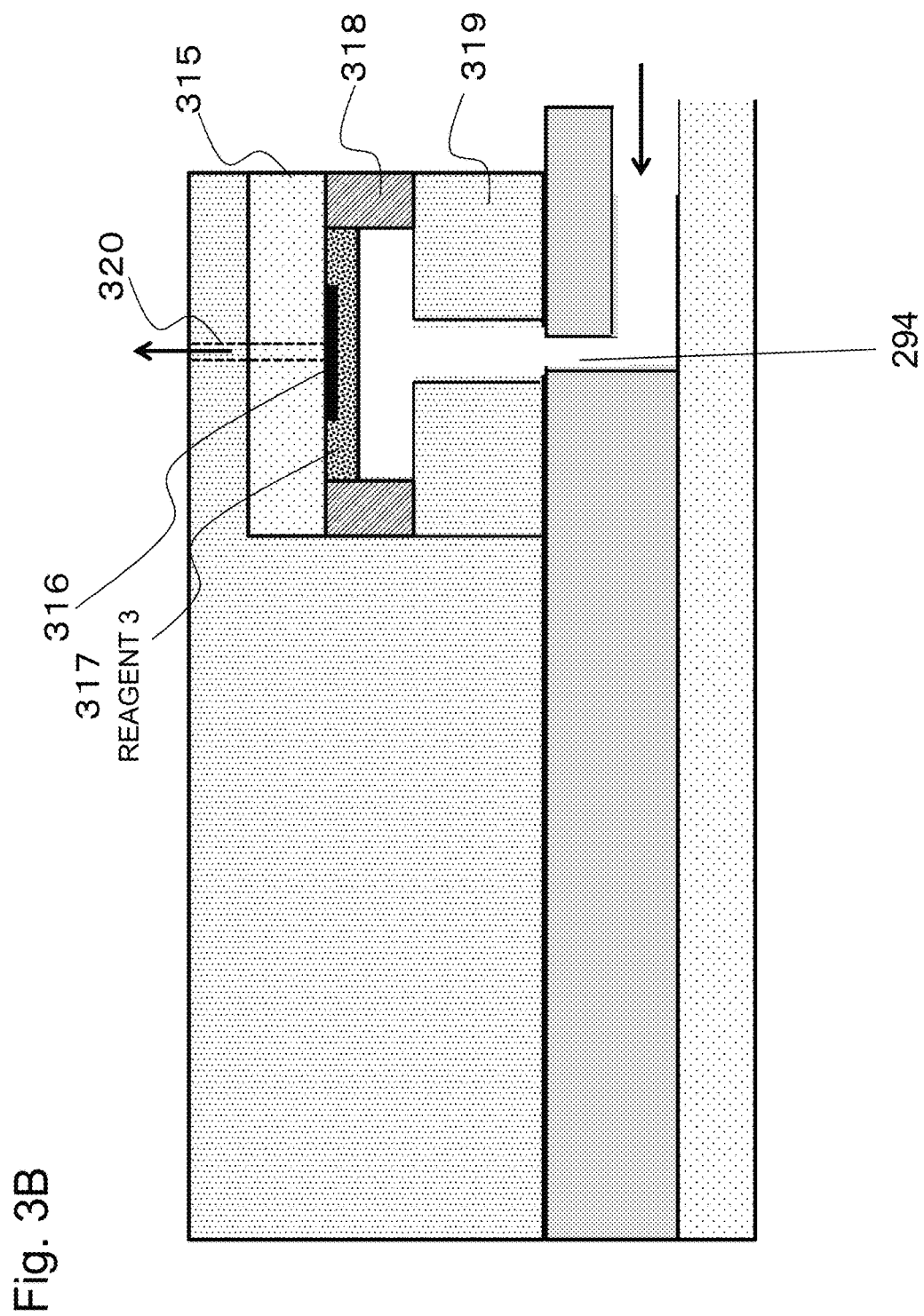
FIG. 3B is a sectional schematic view showing the components of the DNA chip with micro-channel for DNA analysis according to the present disclosure, the sectional view including a sensor.

FIGS. 3A and 3B are sectional schematic views showing components of the DNA chip with micro-channel for DNA analysis according to the present disclosure.

FIG. 3A is a sectional view including a reagent, a pump and a valve. A pump 310 and a valve 311 are embedded in a plastic section 302, and easily attached and detached. An actuator 312 of a driving section of the pump, for which a piezo element or a polymer actuator may be used, is arranged such that a membrane 313 can be moved up and down. Given that the chip is disposable, for example, a polymer actuator may be used. As shown in the figure, they are connected to a port and a channel formed of silicon of the lower surface, so that liquid delivery can be performed within the silicon layer 301. The micro-channel of the silicon layer 301 is patterned from the lower surface by photolithography and RIE. For tightly closing the patterned channel, a Pyrex glass 314 is used as a lid. The Pyrex glass 314 is bonded to the silicon surface using an anodic oxidation method. For connecting micro-channels of plastic and silicon, a through-hole 308 is formed from the upper surface before the plastic layer 302 is bonded.

FIG. 3B is sectional view of an area including a sensor. A sensor chip 315 is arranged such that a detection surface 316 faces downward. For example, a sensor chip 317 is in a detachably attachable state. Further, the detection surface may be dry-chemically treated with the reagent (3) and held in a cavity 318. When the distance between the sensor chip and the silicon chip is long, a spacer 319 may be provided. An air hole 320 may be provided on the upper surface because degassing is necessary at the time of liquid delivery to the cavity of the sensor.

Figure 4:
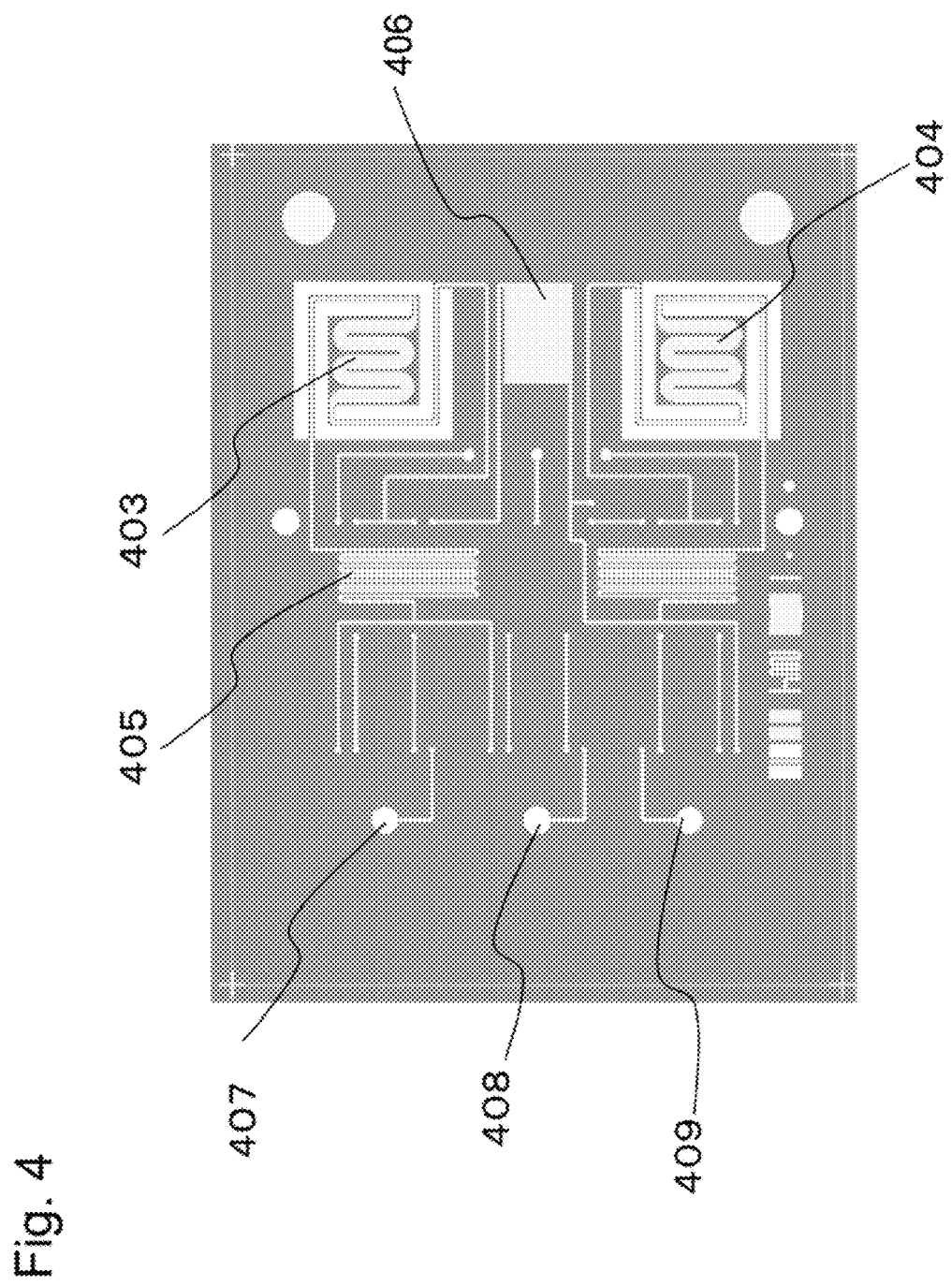
FIG. 4 is a layout view of components included in a silicon chip of the present disclosure.

FIG. 4 is a layout view of components included in a silicon chip used in the embodiment of the present disclosure.

The thickness of the silicon substrate, for example, may range about 500 to 800 μm. The parts are etched from the upper surface and the lower surface using two masks. The peripheries of a PCR1: 403 and a PCR2: 404 are mostly etched from both the upper and lower surfaces by RIE to be completely hollowed out, so that the PCRs are thermally isolated. On the other hand, a channel, a mixer 405 and a micro-sieve 406 are formed by etching the lower surface to a depth of about 300 μm by RIE, and a Pyrex glass is anodic oxidation-bonded to cover the surface. Through-holes of connection areas between holes 407, 408 and 409 and the plastic section are formed by etching the upper surface to a depth of about 300 μm by RIE.

Figure 5:
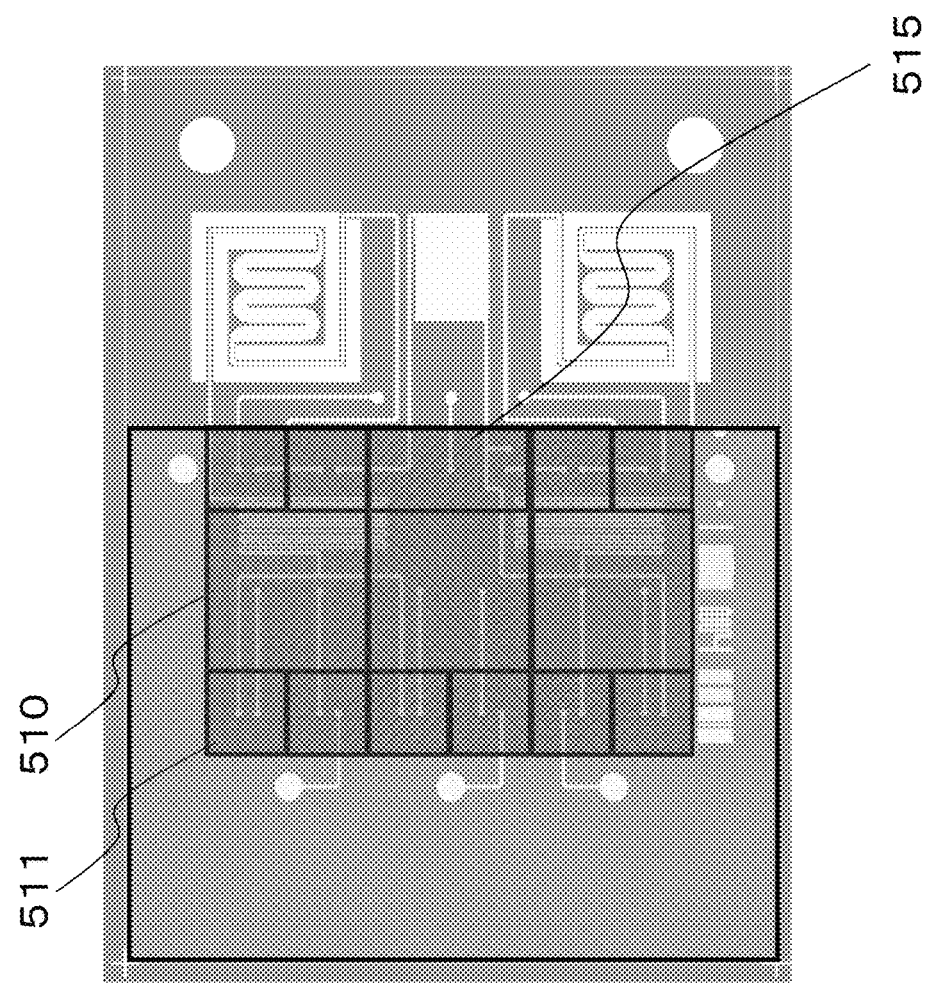
FIG. 5 is a layout view of components included in a plastic chip of the present disclosure.

FIG. 5 is a layout view of components included in a plastic chip of the present disclosure. A pump of a polymer actuator is mounted at the location of symbol 510, and a valve of the polymer actuator is mounted at the location of symbol 511. A sensor is connected at the location of symbol 515.

Figure 6B:
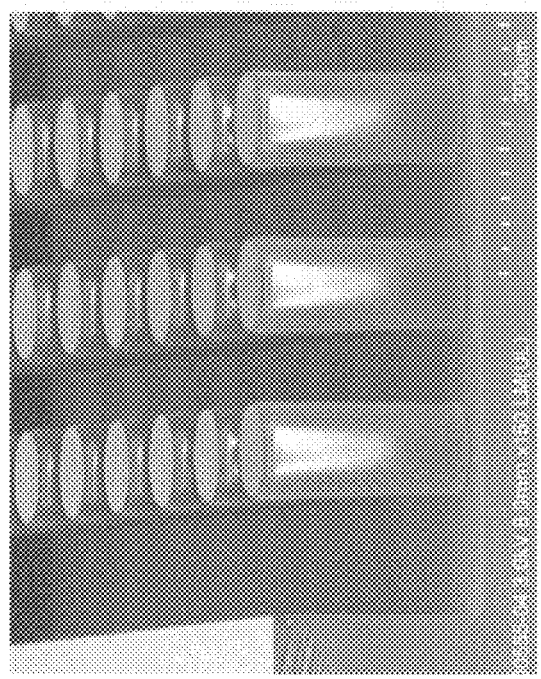
FIG. 6B shows a SEM photograph of a filter obtained using the method of the present disclosure.
Figure 6A:
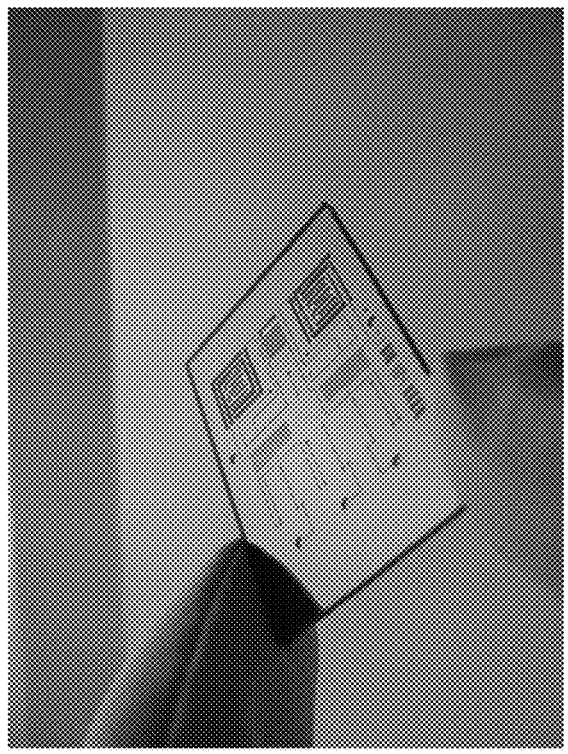
FIG. 6A shows a silicon chip obtained using a method of the present disclosure.

FIG. 6A shows a photograph of a silicon chip section in a DNA chip with micro-channel for DNA analysis which is actually prepared in this embodiment. As one example of processing, FIG. 6B shows a photograph of a filter section actually prepared by a method in this embodiment.

Figure 7:
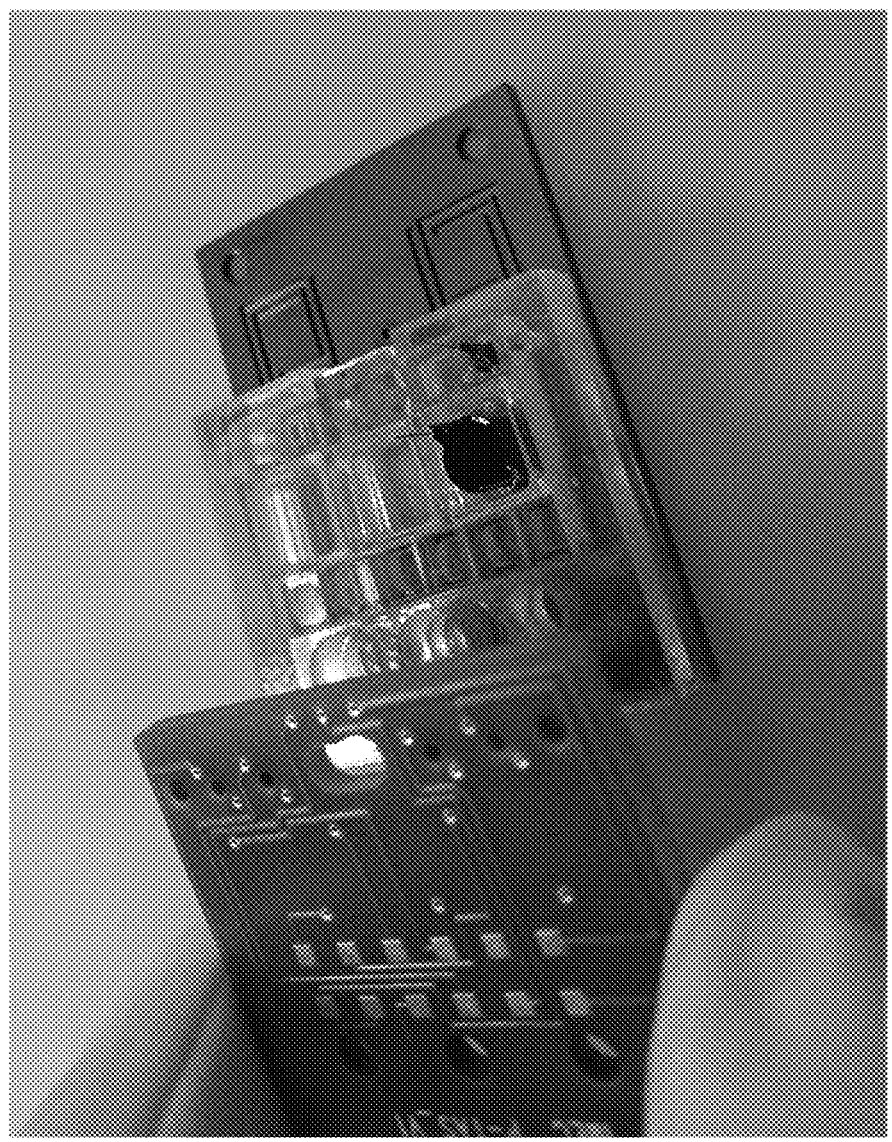
FIG. 7 is a plastic chip obtained using the method of the present disclosure, and a silicon chip bonded thereto.

FIG. 7 shows a photograph of a plastic chip and a silicon chip bonded thereto in a DNA chip with micro-channel for DNA analysis which is actually prepared in this embodiment.

Examples

FIG. 8 shows, in the form of a table, examples of using a DNA chip with micro-chip for DNA analysis in the present disclosure described in the embodiment for four kinds of purposes, respectively. The configurations of reagents will be described below.

(A) Taq-polymerase manufactured by TAKARA BIO INC.: 0.2 μL, PCR mix: 3 μL, water: 2 μL, 2mMdNTP: 1 μL, 10 μM Primer 1: 1 μL, 10 μM Primer 2: 1 μL (sequences of the primers are described in *).
(B) KOD-FX-polymerase manufactured by TOYOBO CO., LTD: 0.2 μL, 2×KOD-Buffer: 5 μL, 2mMdNTP: 1 μL, 10 μM Primer 3: 1 μL, 10 μM Primer 4: 1 μL (sequences of the primers are described in *).
(C) Taq-polymerase manufactured by TAKARA BIO INC.: 0.2 μL, PCR mix: 3 μL, Primer 3': 2 μL, Primer 4: 2 μL, distilled water 10.8 μL (sequences of the primers are described in *).
(D) Tricine buffer solution (pH 8.8) 1.8 μL 45 mM
   oxidized nicotinamide dinucleotide 0.2 μL 1 mM
   magnesium chloride 0.4 μL 1.7 mM
   potassium ferricyanide 2 μL 10 mM
   glyceraldehyde 3-phosphate 0.66 μL 10 mM
   diaphorase 1 μL 10 U/mL
   glyceraldehyde 3-phosphate dehydrogenase 1 μL 32 U/mL
   pyrophosphatase 0.5 μL 5 U/mL

* Primer 1 (5'-ACGGGCTGCAGGCATACACT-3': SEQ ID NO:1), Primer 2 (5'-GGC AGG TCC TGA ACC TC-3': SEQ ID NO:2), Primer 3 (5'-TAGGAAGGATGTCCTCG-3': SEQ ID NO:3), Primer 3' (5'-TAGGAAGGATGTCCTCGT-GACG-3': SEQ ID NO:4) and Primer 4 (5'-TTCTTG ATG-GCAAACACAGTTAAC-3': SEQ ID NO:5)

Examples showing versatility of the DNA chip with micro-channel for DNA analysis in the present disclosure will be described in detail below. The present disclosure is not limited by the following examples.

Example 1

A desired DNA fraction including the 114th base of the 12th exon of an acetaldehyde dehydrogenase 2 (ALDH 2) gene was extracted and amplified from a human genome analyte by using a DNA chip with micro-channel for DNA analysis according to one embodiment of the present disclosure. A DNA fragment with a fraction length of 141 bp was extracted and amplified with the aforementioned Primer 1 and Primer 2 used as primers.

Figure 9:
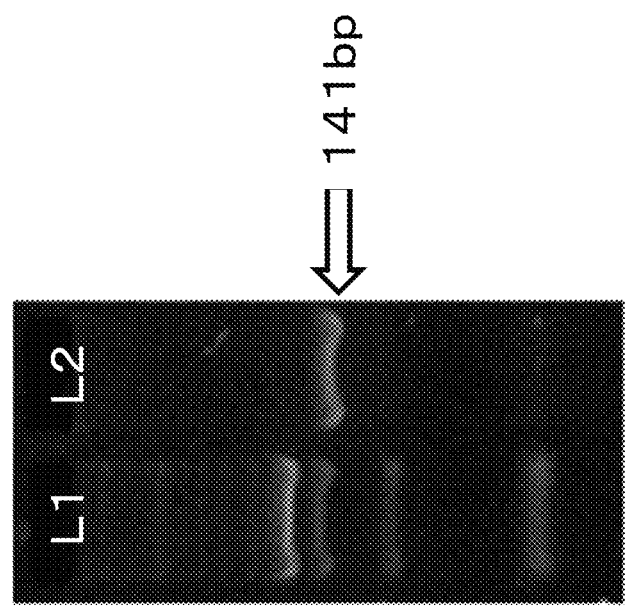
FIG. 9 shows a result of genetic analysis, which is obtained in example 1 of the present disclosure.

The reagent (A) as a reagent 1 was mixed with an analyte in a mixer, and then reaction in a PCR 1 reactor was carried out in 30 cycles of PCR under conditions of 98° C. for 30 seconds, 60° C. for 30 seconds and 68° C. for 30 seconds. Subsequently, the reaction product was made to pass through a filter and a PCR 2 as it was. Three μL of this sample was collected. Subsequently, existence or nonexistence of DNA amplification was checked using an electrophoresis method with agarose gel. The second lane in FIG. 9 corresponds to the result for existence or nonexistence of amplification of the DNA fragment collected from the sample. As shown in the second lane (L2) in FIG. 9, it was confirmed that a desired DNA fragment (141 bp) was amplified.

Example 2

DNA was amplified from a blood analyte by using a DNA chip with micro-channel for DNA analysis according to one embodiment of the present disclosure. As a model of DNA amplification, blood of each of types AB and O was used as a template. A DNA fragment including the 261st base of the sixth exon in a genome in human blood was extracted and amplified. A DNA fragment with a fraction length of 134 or 135 bp was extracted and amplified with the aforementioned Primer 3 and Primer 4 used as primers.

Figure 10:
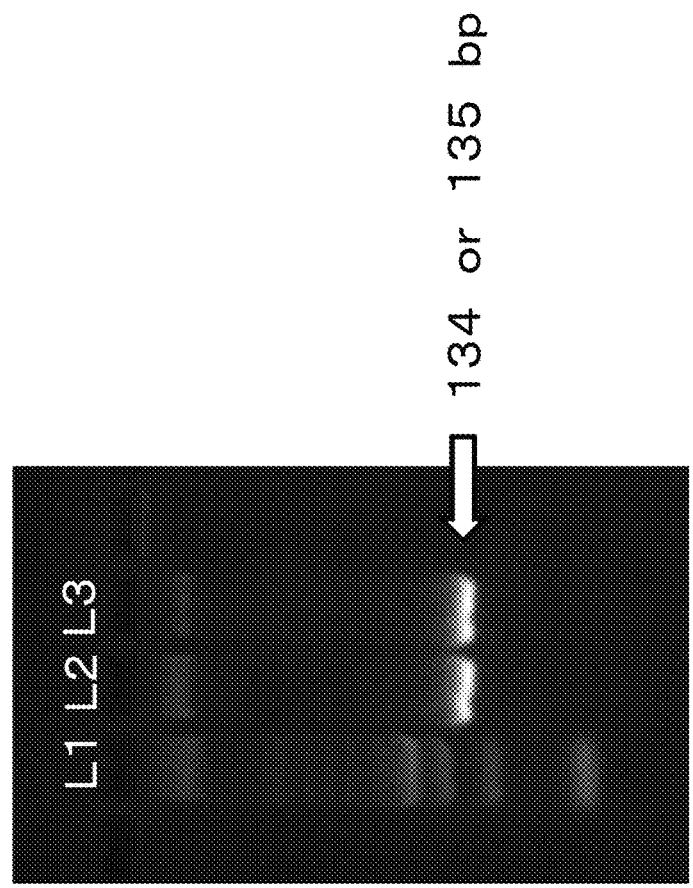
FIG. 10 shows a result of genetic analysis, which is obtained in example 2 of the present disclosure.

The reagent (B) as a reagent 1 was mixed with an analyte in a mixer, and then reaction in a PCR 1 reactor was carried out in 35 cycles of PCR under conditions of 98° C. for 30 seconds, 60° C. for 30 seconds and 68° C. for 30 seconds. Subsequently, the reaction product was made to pass through a filter, and unnecessary blood components fractioned in the PCR reactor were removed. The reaction product was made to pass through a PCR 2 reactor as it was, three μL of this sample solution was collected, and existence or nonexistence of DNA amplification was checked by electrophoresis. The second and third lanes in FIG. 10 correspond to the results for existence or nonexistence of amplification of the DNA fragments collected from the samples of types AB and O, respectively. It was confirmed that DNA was amplified in each of the samples of AB (135 bp) and O (134 bp) as shown in FIG. 10.

Example 3

Allele-specific DNA was amplified from a blood analyte by using a DNA chip with micro-channel for DNA analysis according to one embodiment of the present disclosure. As a model of allele-specific DNA amplification, blood of each of types AB and O was used as a template. The aforementioned Primer 3 and Primer 4 were used as primers for amplifying a DNA fragment including the 261st base (SNP site) of the sixth exon of a human genome. A measurement was performed using Primer 3' and Primer 4 as allele-specific primers for determining a difference in the 261st base (SNP site) of the sixth exon. The allele-specific primer produces an extension reaction specifically only with blood of type AB.

Figure 11:
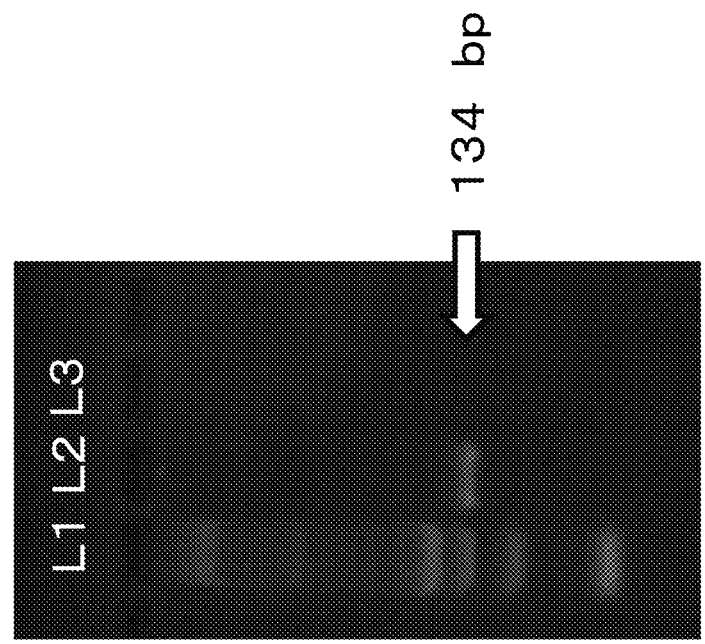
FIG. 11 shows a result of genetic analysis, which is obtained in example 3 of the present disclosure.

The reagent (B) as a reagent 1 was mixed with an analyte in a mixer, and then reaction in a PCR 1 reactor was carried out in 35 cycles of PCR under conditions of 98° C. for 30 seconds, 60° C. for 30 seconds and 68° C. for 30 seconds. Subsequently, impurities were removed with a micro-sieve, and reaction in a PCR reactor 2 was then carried out in 30 cycles of PCR under conditions of 95° C. for 30 seconds, 60° C. for 30 seconds and 72° C. for 30 seconds with the reagent (C) used as a reagent (2). Three μL of this sample solution was collected, and existence or nonexistence of allele-specific DNA amplification was checked by electrophoresis. The second and third lanes in FIG. 11 correspond to the results for existence or nonexistence of amplification of the DNA fragments collected from the samples of types AB and O, respectively. It was confirmed that DNA was specifically amplified in only the sample of the type AB as shown in FIG. 11.

Example 4

An example of detecting a SNP from a blood analyte by using a DNA chip with micro-channel for DNA analysis according to one embodiment of the present disclosure is described.

As a model of SNP detection, blood of each of types AB and O was used as a template as in the case of example 3. The types of primers are same as those in example 3.

Figure 12:
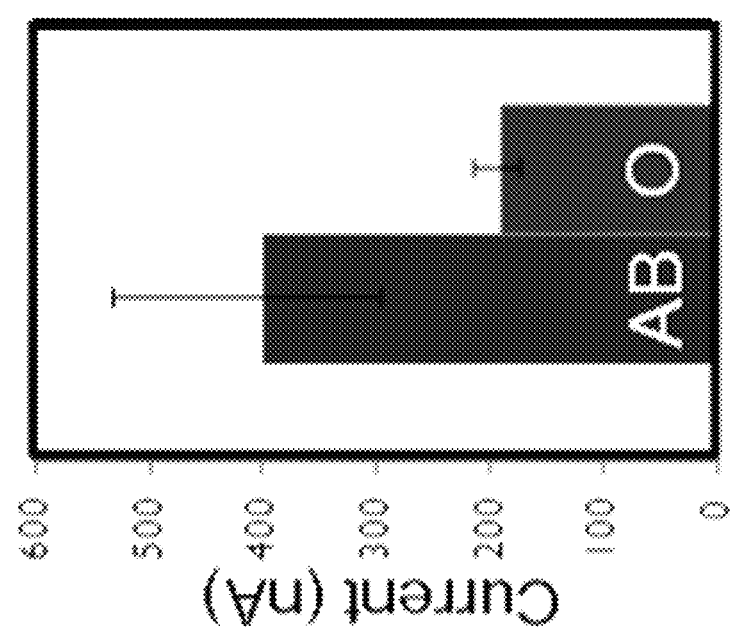
FIG. 12 shows a result of genetic analysis, which is obtained in example 4 of the present disclosure.

The reagent (B) as a reagent 1 was mixed with an analyte in a mixer, and then reaction in a PCR 1 reactor was carried out in 35 cycles of PCR under conditions of 98° C. for 30 seconds, 60° C. for 30 seconds and 68° C. for 30 seconds. Subsequently, the reaction product was made to pass through a filter, freed of unnecessary blood components fractioned in the PCR reactor, and then mixed with a reagent 2 in a mixer 2, the mixture was introduced into a PCR reactor 2, and reaction in the PCR 2 reactor was carried out in 30 cycles of PCR under conditions of 95° C. for 30 seconds, 60° C. for 30 seconds and 72° C. for 30 seconds with the reagent (C) used as the reagent 2. Only 1 μL of this sample solution was delivered to a pyrophosphoric acid sensor, and mixed with a dried reagent (D), and a voltage of 600 mV was applied to a working electrode to measure a voltage value. It was confirmed that since pyrophosphoric acid was generated as a by-product only when allele-specific DNA amplification occurred, a significant difference in current was observed between the types AB and O, so that a SNP could be detected as shown in FIG. 12.

According to the present disclosure, extraction and amplification of DNA or detection of a sequence of the DNA can be performed quickly and conveniently in a DNA chip with micro-channel for DNA analysis, and the chip can be used for a variety of applications, leading to enhancement of versatility. Contribution to personalized medicine can be expected.

The invention claimed is:

1. A DNA chip with micro-channel for DNA analysis of DNA included in an analyte according to PCR method, the DNA chip comprising:
   a first layer made of silicon; and
   a second layer made of plastic,
      wherein the second layer is formed on the first layer, and the second layer is configured to be changeably selected depending on a kind of the analyte and DNA, the first layer includes:
      at least four openings;
      two reactors connected in series,
         wherein a first reactor is configured to extract nucleic acids from a sample in the first reactor and a second reactor configured to selectively amplify DNA,
         wherein each reactor has a thermocycler that increases and decreases the temperature of each reactor, and
         wherein each reactor has a peripheral area made of silicon around each reactor, the peripheral area having a hollowed out shape except for an area connected to the micro-channel;
      at least one filter provided between the first reactor and the second reactor,
         wherein the filter comprises a plurality of column pillars made of silicon formed by etching, a space between column pillars ranging from 1 micro-meters to 10 micro-meters, and the filter separates and removes blood-derived blood cells; and
      a micro-channel connecting among the openings, the first reactor, the second reactor and the filter,
   the second layer includes:
      a pump; and
      a sensor,
      wherein a reagent covers at least one opening included in the four openings when one sees from normal direction of the first layer,
      the pump is located over at least two openings included in the four openings when one sees from normal direction of the first layer,
      the pump supplies the reagent to the reactors via the micro-channel such that mixture of the reagent and the analyte is supplied to the reactors,
      the mixture is transported to the sensor via at least one opening included in the four openings such that the sensor analyzes DNA included in the analyte.

2. The DNA chip according to claim 1, wherein a polymer actuator is used as a pump.

3. DNA analysis method of DNA included in an analyte according to PCR method by using a DNA chip with a micro-channel, the method comprising:
   (a') providing the DNA chip of claim 1
      wherein a reagent covers at least one opening included in the four openings when one sees from normal direction of the first layer,
      the pump is located over at least two openings included in the four openings when one sees from normal direction of the first layer,
   (d) supplying the analyte to the reactors;
   (e) supplying the reagent to the PCR reactors via the micro-channel by using the pump such that mixtures of the reagent and the analyte are supplied to the PCR reactors;
   (f) performing PCR method to obtain PCR products;
   (g) transporting the PCR products to the sensor via at least one opening included in the four openings; and
   (h) detecting the PCR products by using the sensor to analyze DNA included in the analyte.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
acgggctgca ggcatacact                                          20

<210> SEQ ID NO 2
<211> LENGTH: 17
<212> TYPE: DNA
<213> ORGANISM: Artificial Sequence
<220> FEATURE:
<223> OTHER INFORMATION: primer

<400> SEQUENCE: 2 ggc agg tcc tga acc tc                                         17

<210> SEQ ID NO 3
<211> LENGTH: 17
<212> TYPE: DNA
<213> ORGANISM: Artificial Sequence
<220> FEATURE:
<223> OTHER INFORMATION: primer

<400> SEQUENCE: 3
taggaaggat gtcctcg                                             17

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
taggaaggat gtcctcgtga cg                                       22

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
ttcttgatgg caaacacagt taac                                     24